(12) United States Patent
Arenberg et al.

(10) Patent No.: US 6,648,873 B2
(45) Date of Patent: Nov. 18, 2003

(54) AURAL CATHETER SYSTEM INCLUDING ANCHOR BALLOON AND BALLOON INFLATION DEVICE

(75) Inventors: Michael H. Arenberg, Los Gatos, CA (US); Edward M. Gillis, Cupertino, CA (US); Charles R. Rampersaud, Cupertino, CA (US)

(73) Assignee: Durect Corp., DE (US)

( * ) Notice: Subject to any disclaimer, the term of this patent is extended or adjusted under 35 U.S.C. 154(b) by 70 days.

(21) Appl. No.: 09/960,558

(22) Filed: Sep. 21, 2001

(65) Prior Publication Data

US 2003/0060799 A1 Mar. 27, 2003

(51) Int. Cl.⁷ ............................................. A61M 31/00
(52) U.S. Cl. .................................... 604/509; 604/96.01
(58) Field of Search ................................ 604/20, 891.1, 604/892.1, 96.01, 97.01, 99.01, 500, 506, 507, 508, 509, 514

(56) References Cited

U.S. PATENT DOCUMENTS

| | | | |
|---|---|---|---|
| 2,642,065 A | 6/1953 | Negri | |
| 3,528,419 A | 9/1970 | Joechle et al. | |
| 4,034,759 A | 7/1977 | Haerr | |
| 4,159,719 A | 7/1979 | Haerr | |
| 5,219,334 A | * 6/1993 | Tsukada | 604/132 |
| 5,421,818 A | 6/1995 | Arenberg | |
| 5,474,529 A | 12/1995 | Arenberg | |
| 5,476,446 A | 12/1995 | Arenburg | |
| 6,045,528 A | 4/2000 | Arenberg et al. | |
| 6,440,102 B1 | * 8/2002 | Arenberg et al. | 604/96.01 |

* cited by examiner

Primary Examiner—Brian L. Casler
Assistant Examiner—Kevin C. Sirmons
(74) Attorney, Agent, or Firm—Adam W. Bell

(57) ABSTRACT

Methods and apparatus used for securing the end of a drug-delivery catheter at the round window niche of the inner ear; specifically an apparatus employing a miniature threaded screw pump to inflate a balloon allowing a catheter to be secured within the round window niche of the inner ear.

17 Claims, 4 Drawing Sheets

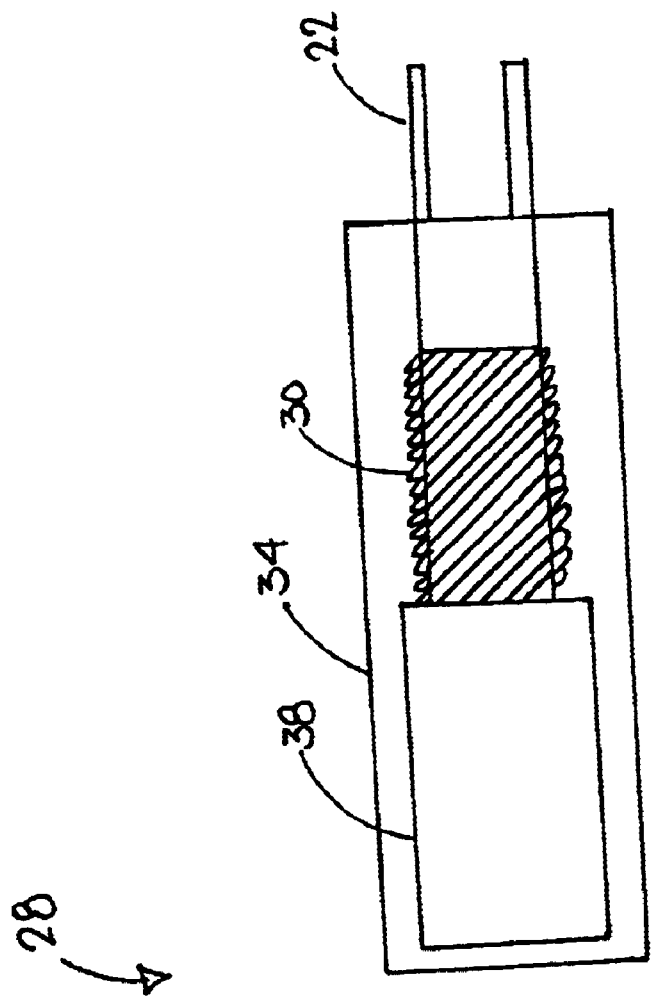
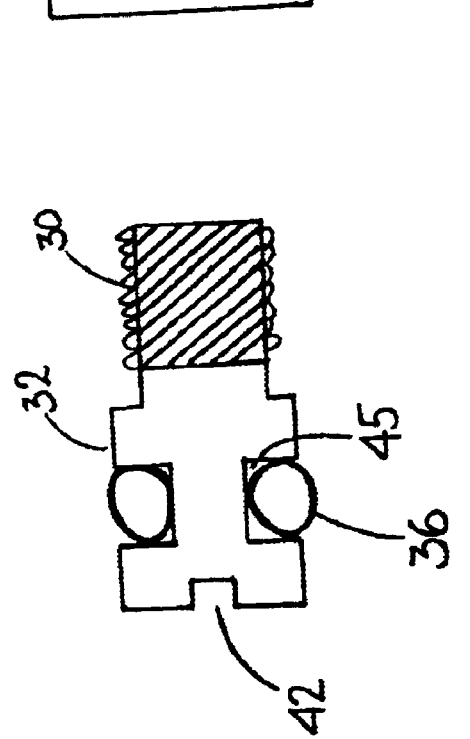
Fig. 6

AURAL CATHETER SYSTEM INCLUDING ANCHOR BALLOON AND BALLOON INFLATION DEVICE

FIELD OF THE INVENTION

The invention relates to therapeutic treatment of the inner ear. Particularly, methods and apparatus are described that may be used in locating and securing the end of a drug-delivery catheter at the round window niche of the inner ear. Specifically the invention relates to an apparatus and methods that employ a miniature threaded screw pump to inflate a balloon that allows a catheter to be secured within the round window niche of the inner ear.

BACKGROUND OF THE INVENTION

The present invention generally relates to a multi-functional medical apparatus for use in connection with the inner ear wherein the apparatus is capable of (1) delivering therapeutic agents to internal ear (e.g. inner ear) structures; (2) withdrawing fluid materials from the inner ear; (3) causing temperature, pressure and/or volumetric changes in the fluids and fluid chambers of the inner ear; and (4) enabling internal (e.g. inner) ear structures to be electro-physiologically monitored.

See U.S. Pat. Nos. 5,421,818; 5,474,529 and 5,476,446, each titled Multi-Functional Inner Ear Treatment and Diagnostic System, each to Irving K. Arenberg, and U.S. Pat. No. 6,045,528, titled Inner Ear Fluid Transfer and Diagnostic System, to Arenberg et al., all of which are expressly incorporated by reference.

In order to treat various ear disorders, it may often be necessary to deliver therapeutic agents to inner and middle ear tissues in a rapid and efficient manner. For example, a variety of structures have been developed which are capable of delivering/administering therapeutic agents into the external auditory canal of the outer ear. U.S. Pat. No. 4,034,759 to Haerr discloses a hollow, cylindrical tube manufactured of sponge material (e.g. dehydrated cellulose) that is inserted into the external auditory canal of a patient. When liquid medicines are placed in contact with the tube, it correspondingly expands against the walls of the auditory canal. As a result, accidental removal of the tube is prevented. Furthermore, the medicine absorbed by the tube is maintained in contact with the walls of the external auditory canal for treatment purposes. Haerr does not disclose an inflatable balloon used to secure a catheter in the round window niche of the inner ear.

Other absorbent devices for treatment of the auditory canal and related tissue structures are disclosed in U.S. Pat. No. 3,528,419 to Joechle, U.S. Pat. No. 4,159,719 to Haerr, and U.S. Pat. No. 2,642,065 to Negri.

The Negri patent specifically discloses a medicine delivery device with an internally mounted, frangible medicine container which, when broken, releases liquid medicines into an absorbent member. However, the delivery of therapeutic agents in a controlled and effective manner is considerably more difficult with respect to tissue structures of the inner ear (e.g. those portions of the ear contained within the temporal bone which is the most dense bone tissue in the entire human body), particularly because it is difficult to deliver and maintain a drug in contact with the round window of the inner ear. Exemplary inner ear tissue structures of primary importance include but are not limited to the cochlea, the endolymphatic sac/duct, the vestibular labyrinth, and all of the compartments which include these components. Access to the foregoing inner ear tissue regions is typically achieved through the round window membrane, or alternatively through the oval window/stapes footplate, and the annular ligament. The middle ear shall be defined as the physiological air-containing tissue zone behind the tympanic membrane (e.g. the ear drum) and ahead of the inner ear. It should also be noted that access to the inner ear may be accomplished through the endolymphatic sac/endolymphatic duct and the otic capsule.

The foregoing inner ear tissues are of minimal size, and only readily accessible through microsurgical procedures. In order to treat various diseases and conditions associated with these and other inner ear tissues, the delivery of medicines thereto is often of primary importance as previously noted.

One particularly problematic aspect of treatments delivering drugs to the inner ear, particularly via the round window, is the difficulty of effectively placing a delivery catheter against the round window for a prolonged period of time, such as for a day, a week, or a month. This has proved difficult since the expulsion of a drug from the end of the catheter tends to dislodge the catheter from its place against the round window niche, and the drug formulation itself, which may be oily, only serves to undermine the positional stability of the catheter. There is a need for a device that can easily and practically be used to fix in place a catheter against the round window niche so that the catheter may be used to deliver a drug over a protracted period, such as a week or month or more.

Exemplary medicines which are typically used to treat inner ear tissues include but are not limited to urea, mannitol, sorbitol, glycerol, xylocaine, epinephrine, immunoglobulins, sodium chloride, steroids, heparin, hyaluronidase, aminoglycoside antibiotics (streptomycin/gentamycin), and other drugs, biological materials, and pharmaceutical compositions suitable for treating tissues of the human body.

Likewise, treatment of inner ear tissues and/or fluids may involve altering the pressure, volumetric, and temperature characteristics thereof. Specifically (as will be described in greater detail below), a precise balance must be maintained with respect to the pressure of various fluids within the inner ear and its associated compartments. Imbalances in the pressure levels of such fluids can cause various problems, including but not limited to conditions known as endolymphatic hydrops, endolymphatic hypertension, perilymphatic hypertension, and perilymphatic hydrops.

The present invention may be used with any number of specially-designed treatment units are disclosed which are capable of performing a wide variety of therapeutic functions including but not limited to (1) the controlled, repeatable, and sustained delivery of therapeutic agents directly into the inner ear or at selected middleinner ear interface tissues; (2) the measurement of inner ear electrical potentials (evoked or otherwise) using a technique known as "electrocochleography" (hereinafter "ECoG") which is described in greater detail below; (3) the alteration of temperature, volume and pressure conditions within the inner ear; and (4) the controlled withdrawal of inner ear fluid materials.

Accordingly, the present invention encompasses methods and apparatus that employ a miniature threaded screw pump to inflate a balloon wherein the balloon is communicably attached at or adjacent to a distal end of a catheter, and represents an advance in the art of inner ear treatment and drug delivery as described in detail below.

SUMMARY OF THE INVENTION

Aspects of the present invention includes methods and apparatus that employ a miniature threaded screw pump to inflate a balloon wherein the balloon is communicably attached at or adjacent to a distal end of a catheter. The pump may employ a threaded interface to drive a piston head relative to a pump housing. The catheter is used to deliver fluids to (and from) the inner ear, and the balloon is adapted to hold the catheter securely at the round window niche of the inner ear. The balloon may take any number of forms, from substantially spherical to an ovoid or toroid shape. It may be located coaxially with the distal end of the catheter or in an offset fashion.

Preferably, the balloon is configured to fit within the round window niche of a patient and be secured upon at least partial inflation. However, the overall structure described may be modified for use in other orifices or apertures. A inflation lumen may be provided to inflate the balloon, whereas at least one delivery lumen may be provided to deliver therapeutic agent to a treatment site or to drain fluid from a treatment site.

The present invention has the advantage that it can be easily, cheaply and practically be used to removably fix in place a catheter against the round window niche so that the catheter may be used to deliver a drug over a protracted period, such as several days, or a week or a month or more. The balloon may be inflated using the screw pump to secure the catheter in the round window niche, and, periodically, the amount of inflation may be adjusted to make sure that the catheter remains in place. When treatment is finished, the catheter may simply and gently be removed by deflation of the balloon. The use of a miniature screw pump allows very fine adjustments to the amount of balloon inflation.

Another advantage of the present invention is that the use of the miniature screw pump allows minute and accurate adjustments in inflation and deflation of the balloon, such that the drug delivery apparatus may be properly retained in the ear over a period of time without causing unpredictable or uncomfortably great pressure against the round window niche of the inner ear.

Particularly, the present invention includes at least each of the following variations:

1. An apparatus for delivery of a therapeutic agent to the round window of the inner ear, the apparatus comprising: an inflation lumen having a proximal end and a distal end, and at least one delivery lumen having a proximal end and a distal end, the distal end of the inflation lumen being in fluid communication with an expandable balloon member adapted to fit and be secured within the round window niche of the inner ear, the proximal end of the inflation lumen being in fluid communication with a miniature pump, the distal end of the delivery lumen being positioned to allow delivery of the therapeutic agent to the round window of the inner ear when the balloon is secured within the round window niche.
2. Apparatus described in (1), wherein the miniature pump is a screw pump employing a threaded interface to drive a piston head relative to a pump housing.
3. The apparatus described in (2) wherein the miniature screw pump comprises a piston, a housing and a threaded interface for driving the piston within the housing.
4. The apparatus described in (3) wherein the miniature screw pump has a displacement of between about 0.5 microliters and 100 microliters.
5. The apparatus described in (4) wherein the miniature screw pump has a displacement of between about 1 microliter and 50 microliters.
6. The apparatus described in (5) wherein the miniature screw pump has a displacement of between about 1 microliter and 25 microliters.
7. The apparatus described in (3) wherein the inflation lumen contains a fluid and wherein balloon inflation is accomplished by displacement of the fluid by means of the miniature screw pump.
8. The apparatus described in (7) wherein the fluid is a viscous fluid.
9. The apparatus described in (8) wherein the viscous fluid is selected from the group consisting of: silicone, an oil, a sugar solution and a polymer.
10. A method for delivering a therapeutic agent to the round window of the inner ear, comprising introducing into the ear an apparatus, the apparatus comprising: an inflation lumen having a proximal end and a distal end, and at least one delivery lumen having a proximal end and a distal end, the distal end of the inflation lumen being in fluid communication with an expandable balloon member adapted to fit and be secured within the round window niche of the inner ear, the proximal end of the inflation lumen being in fluid communication with a miniature pump, wherein the inflation lumen contains a fluid and wherein balloon inflation is accomplished by displacement of the fluid by means of the miniature pump, and wherein the distal end of the delivery lumen is positioned to allow delivery of the therapeutic agent to the round window of the inner ear when the balloon is secured within the round window niche, and, by means of the miniature pump, inflating the balloon to secure it within the round window niche of the inner ear, and delivering a therapeutic agent through the catheter the round window of the inner ear.
11. The method as described in (10), wherein the miniature pump comprises a miniature screw pump, wherein said miniature screw pump comprises a piston, a housing and a threaded interface for driving the piston within the housing.
12. The method as described in (11), wherein the miniature screw pump has a displacement of between about 0.5 microliters and 100 microliters.
13. The method as described in (12), wherein the miniature screw pump has a displacement of between about 1 microliter and 50 microliters.
14. The method as described in (13), wherein the miniature screw pump has a displacement of between about 1 microliter and 25 microliters.
15. The method described in (11) wherein the fluid is a viscous fluid.
16. The method described in (15) wherein the viscous fluid is selected from the group consisting of: silicone, an oil, a sugar solution and a polymer.

In addition to the inventive variations just described, it is contemplated that each component, or the components taken together may have further applicability beyond that described. Of course, the devices as well as the methodology described herein form aspects of the present invention.

BRIEF DESCRIPTION OF THE DRAWINGS

Each of the following figures provide examples diagrammatically illustrating aspects of the present invention. Like elements in the various figures are indicated by identical numbering. For the sake of clarity, some such numbering may be omitted.

FIG. 6 is an enlarged cross-sectional view of the pump end of the catheter taken along the line II—II.

DETAILED DESCRIPTION OF THE INVENTION

Preamble

Figure 1:
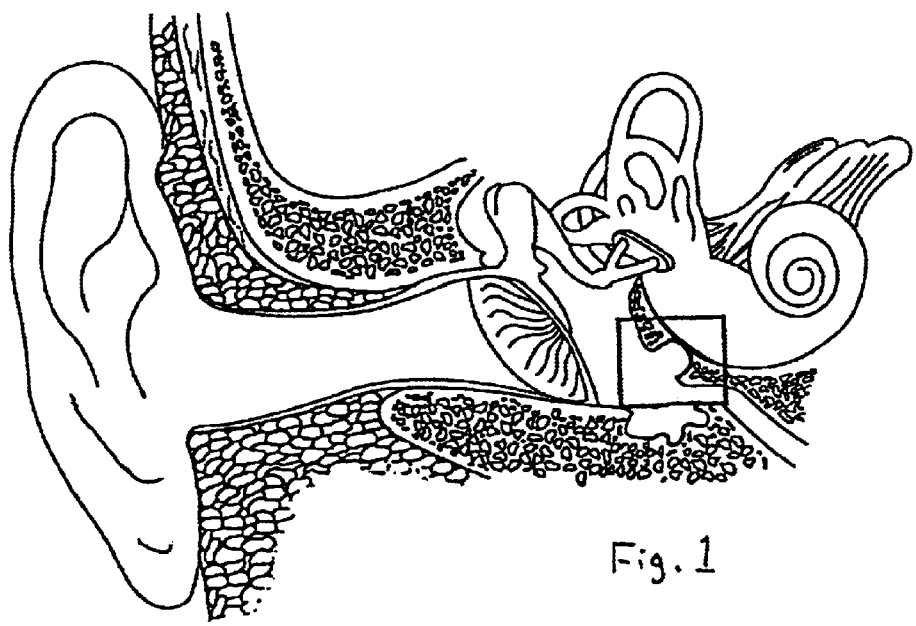
FIG. 1 shows the gross anatomy of a human ear.

Before the present invention is described, it is to be understood that this invention is not limited to particular variations described, as such it may, of course, vary. It is also to be understood that the terminology used herein is for the purpose of describing particular variations only, and is not intended to be limiting, since the scope of the present invention will be limited only by the appended claims.

Where a range of values is provided, it is understood that the range includes values encompassing a half integer either side of the stated range. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. The publications discussed are provided solely for their disclosure prior to the filing date of the present application. Nothing herein is to be construed as an admission that the present invention is not entitled to antedate such publication by virtue of prior invention.

As used herein and in the appended claims, the singular forms "a", "and", and "the" include plural referents unless the context clearly dictates otherwise. Conversely, it is contemplated that the claims may be so-drafted to exclude the inclusion of more that an single element. This statement is intended to serve as antecedent basis for use of such exclusive terminology as "solely," "only" and the like in connection with the recitation of any claim element. Furthermore, it is contemplated that any element indicated to be optional in this Specification may be specifically excluded from a given claim, treating the same as a "negative" limitation. Last, it is noted that it is contemplated that any optional feature of the inventive variations described herein may be set forth and claimed independently, or in combination with any one or more of the features described herein.

Definitions

"Inflation lumen" refers to the lumen or tube that is used to inflate and deflate the balloon. The inflation lumen will generally be attached at one end to a balloon and at the other end to the miniature screw-type pump. The inflation lumen generally is filled with a liquid or gaseous fluid, which may be a viscous fluid such as silicone. By actuation of the miniature pump, fluid is displaced within the inflation lumen and forced into the balloon, thereby inflating it.

"Delivery lumen" refers to the lumen or tube via which a fluid such as a therapeutic agent, (e.g. an antibiotic such as gentamicin or a corticosteirod) is delivered to the inner ear. The delivery tube may alternatively function to transport fluid from the inner ear to the outside, i.e. to drain fluid from the ear. In certain embodiments, it may be advantageous to have two or more delivery lumens, wherein one may serve to deliver a fluid to the inner ear and the other may serve to drain fluid from the inner ear.

"Expandable balloon member" refers to any device that may be expanded by creating an internal pressure. Generally the expandable balloon member will be a baglike device made from an elastic substance that may be inflated by forcing a gaseous or liquid fluid into the interior of the balloon. Likewise the balloon may be deflated by releasing the pressure.

"Therapeutic agent" includes any substance meant to affect animal physiology, for example an antibiotic such as gentamicin or streptomyacin, or a corticosteroid or other agents such as urea, mannitol, sorbitol, glycerol, xylocaine, epinephrine, immunoglobulins, sodium chloride, steroids, heparin or hyaluronidase.

A "viscous" fluid as used herein means any fluid having a viscosity greater than that of pure water.

The word "secured" as used herein, e.g. referring to a balloon secured within the round window niche of the inner ear, means placed to that the balloon will stay where put, at least for a reasonable amount of time depending upon the required utility, and not be dislodged therefrom by normal movement of the subject. The term is not meant to imply that the balloon completely occludes the round window niche of the inner ear, nor does it imply a permanent emplacement.

"Fluid" encompasses any liquid or gaseous substance.

The Figures and Detailed Description

FIG. 1 is an illustration of relevant anatomy of the ear, showing the outer ear canal, the ear drum, the middle ear with the round window niche clearly visible and the inner ear showing the shell-like cochlear structure.

Figure 2:
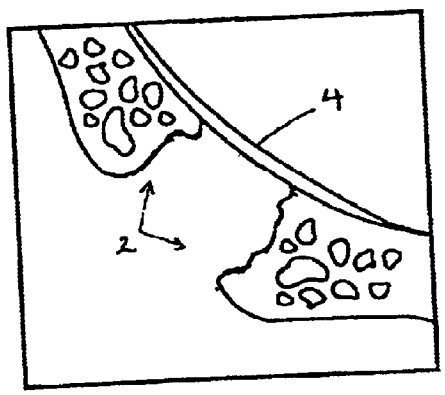
FIG. 2 shows detail of the round window niche of the inner ear.

FIG. 2 shows a detail of the round window niche (2) and round window membrane (4).

Figure 3:
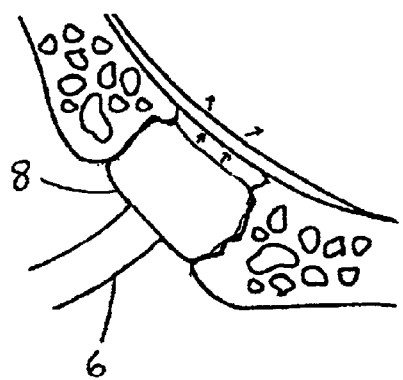
FIG. 3 shows detail of the round window niche with the balloon end of the inventive catheter secured therein.

FIG. 3 shows the distal end of a catheter (6) according to the present invention positioned for use. The balloon (8) is shown fitting within and pressed against features of the round window. Preferably, the balloon has an ovoid, circular, elliptical or toroid shape. It may be located coaxially with the distal end of the catheter or in an offset fashion. Great variability of the shape of the balloon is contemplated in order to compliment the varied and, often, irregular anatomical shape of the round window. Still, however configured, balloons used according to the present invention are preferably adapted/configured to interface with a patient's round window niche and secure the distal end of a catheter therein upon full or partial inflation, with or without sealing the round window niche.

Figure 4:
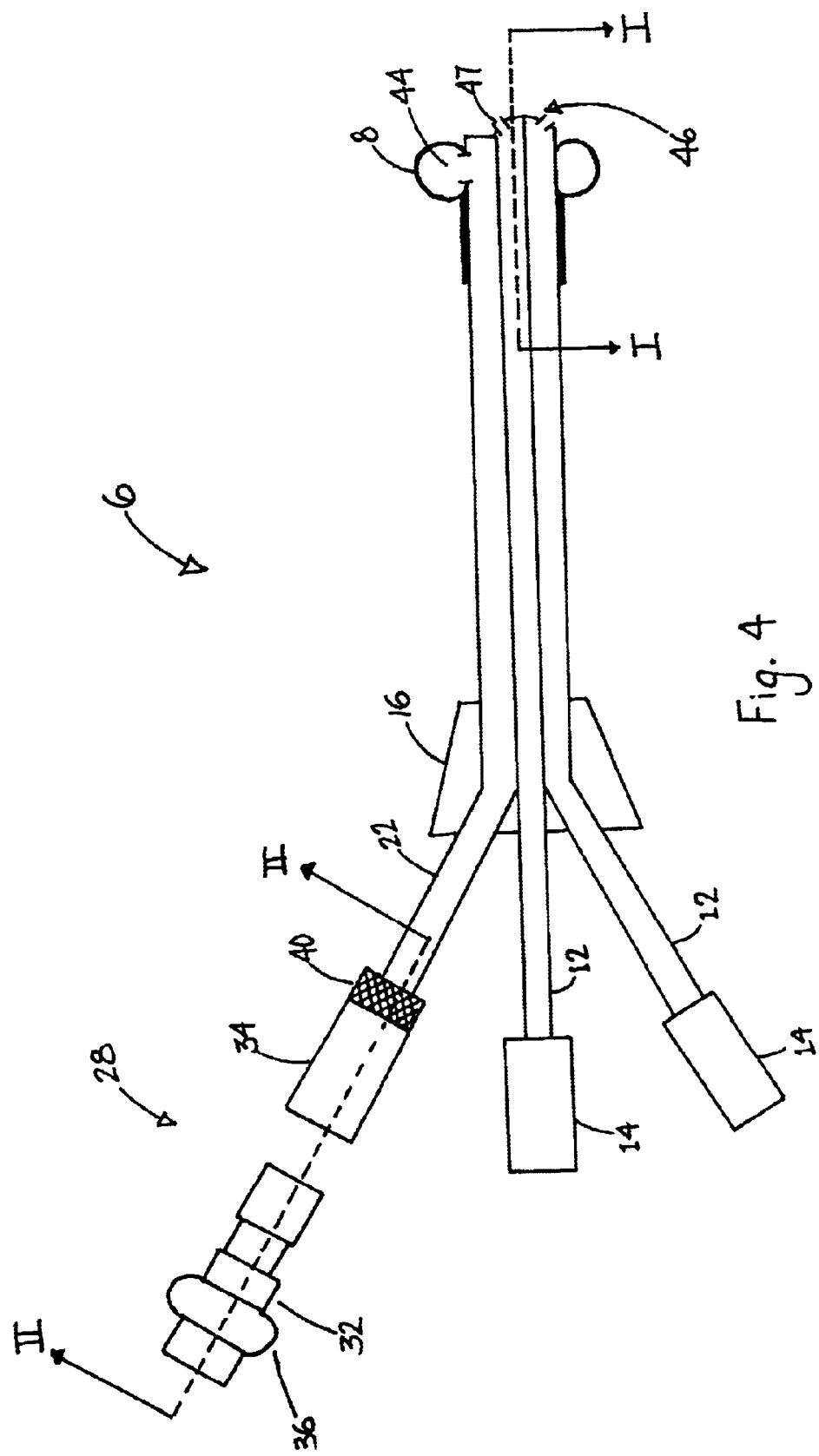
FIG. 4 shows features of a catheter system of the invention.

FIG. 4 shows primary features of the balloon catheter system disclosed. The catheter system (6) may include an inflation lumen (22) and one (or more) delivery lumens (12). The inflation lumen may be concentric to the delivery lumen, or may run parallel to the delivery lumen. Each delivery lumen preferably includes a fitting (14) for interfacing to a drug delivery apparatus. Note that the delivery lumens can be used not only for delivery of a therapeutic agent, but also for removing a fluid, i.e. draining fluid from the inner ear. Also, in certain embodiments, the invention may also include one or more fiber-optic cables that allow illumination and visualization beyond the distal end of the catheter, aiding in positioning of the catheter. The inflation and delivery lumens may be made of polyurethane, polyethylene or silicone or any other suitable material. The balloon may be made of any number of substances that are sufficiently elastic to allow inflation and deflation according to the invention, such materials include, but are not limited to, polyurethane, polyethylene, silicone, plastics, PET, rubber, latex and mixtures thereof, or any other suitable material. In the variation of the invention shown, a junction (16) is proved in which a proximal section of the inflation lumen (22) and proximal sections of the delivery lumen(s) (12) are captured. From the junction, distal sections of the delivery lumen (12) continue as does the distal section of the inflation lumen (22). Junction (16) preferably comprises a resilient material, including those discussed above for the catheter and balloon, thereby enable a simple press-fit assembly procedure for the components shown. Conventional assembly techniques are used in producing the catheters according to the present invention. For instance, the balloon end can be made by skiving the end of a inflation lumen (22) with a razor blade and then bonding material over the top of the lumen adjacent the skive. For such a configuration, the skive (44) functions as an inflation/deflation port to the balloon (8). Also shown in FIG. 4 is the screw pump (28) positioned at the proximal end of the inflation lumen (22). A balloon (8) is shown attached to the distal end of the catheter (6). The interior of the balloon (8) is in fluid communication with the inflation lumen (22).

Figure 5:
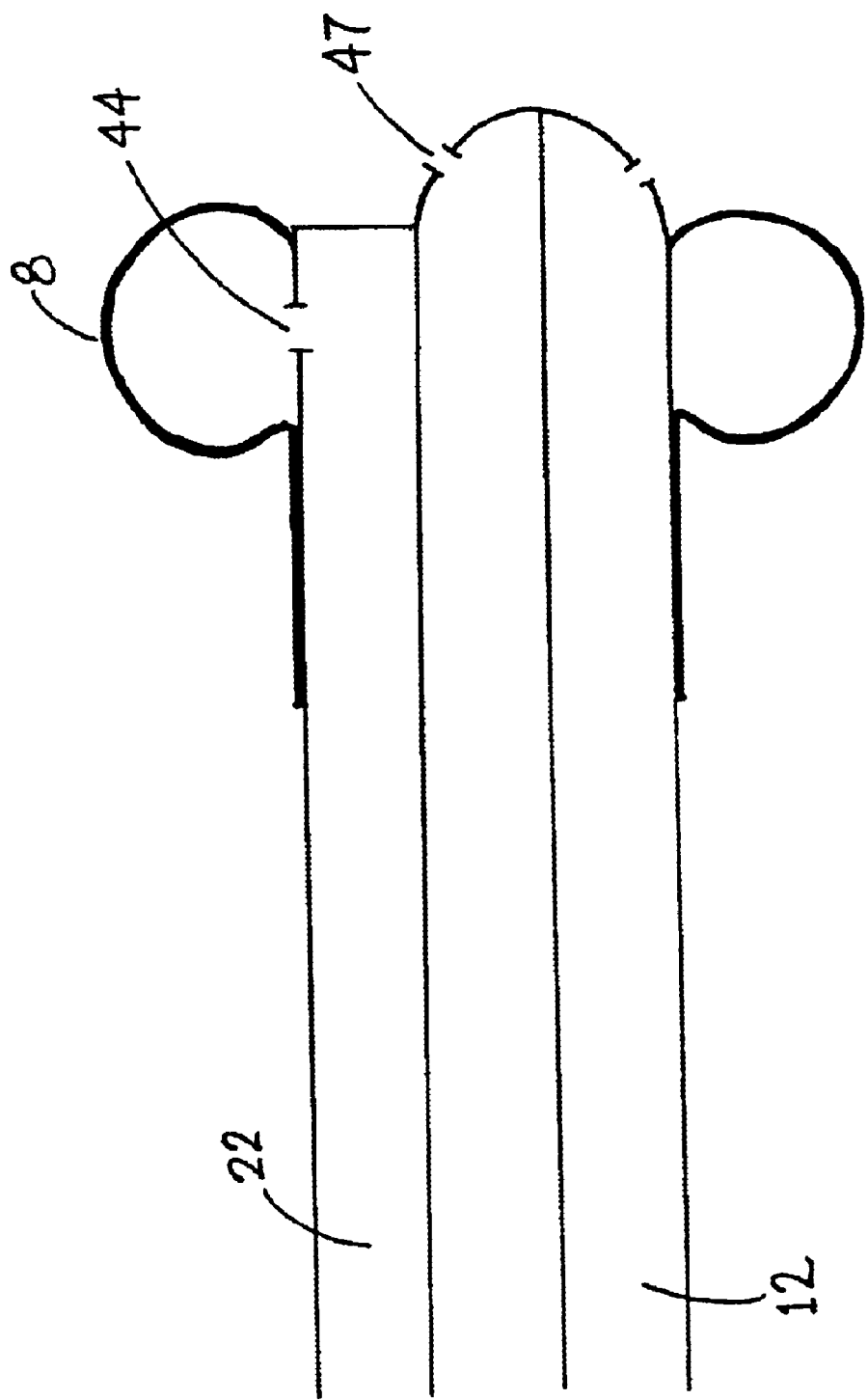
FIG. 5 is an enlarged cross-sectional view of the balloon end of the catheter taken along line I—I.

FIG. 5 shows a view taken along line I—I that shows an enlarged cross-sectional view of the distal end of the catheter (6) showing detail of the inflation lumen (22), the delivery lumen (12), the balloon (8) and the skive (44) in he inflation lumen. Fluid (a liquid or a gas) passes from the inflation lumen (22), through the skive (44), into the balloon (8), thereby inflating the balloon (8). The balloon may be bonded to the outside of the catheter using a conventional mechanical, thermal or adhesive means. Fluid is preferably employed for manipulation of the balloon. Less viscous fluids such as saline or water may be used. Alternately, the inflation lumen (22) and balloon (8) may contain a more viscous fluid such as silicone or an oil or a gel. Using a more viscous material may provide certain advantages in connection with tactile feedback upon balloon inflation, improved compliance with the target round window site, and may extend the period during which the balloon remains inflated. FIG. 5 also shows two delivery lumens (12), and a fenestrated delivery head (46) having a one or a plurality of pores (47), through which fluid may pass out of or into a delivery lumen (12). A substance, such as a drug, such as gentamicin, may flow up one delivery lumen (12), then out of one or more of the pores (47), into the round window space of the inner ear, where it will have its therapeutic effect. Excess drug may then flow back through a pore (47), through a second delivery lumen (12), and thereby be drained away from the delivery site via the catheter (6).

FIG. 6 shows a miniature pump (28) in fluid communication with the inflation lumen (22). By "miniature," it is meant that the pump has a total displacement between about 0.5 and 100 microliters. In certain embodiments it has a displacement of between about 1 and 25 microliters. Pump displacement volume corresponds to the volume required for a filled balloon (8) to be secured in the round window of a human or other mammalian subject. Operating pressures for pump (28) range between about 1 psi to upward of 300 psi. Preferably, lower pressures in the range of 1 to 20 psi are used. At low pressure, once the balloon has conformed to the anatomy of the round window, resistance to flow provided by highly viscous fill material will help the balloon maintain a secure position upon disturbance. The pump (28) is designed for precise control of fluid delivery to balloon (8). This is accomplished through the use fine pitch screw threads (30) controlling the advance of a piston (32) within a housing (34) wherein the piston and the housing possess complementary screw threads. A housing (34) is attached to the inflation lumen (22) as illustrated in FIG. 6. The inflation lumen may be attached such that it's proximal end fits within the interior space of the pump or such that it is fitted over and around the exterior of the pump body. The attachment of the pump (28) to the inflation lumen (22) may be achieved by any conventional attachment means such as mechanical (such as a sprung clip or wire or memory wire), or adhesive (such as acrylic or epoxy glue) or thermal attachment means. The piston member (32) may include a groove (45) to receive a seal member (36) such as an O-ring. If used, it will run within an optional seal bore (38) thereby making a tight seal between the surface of the O-ring and the interior of the seal bore. In instances where a separate seal member is not used, close tolerance or interfering threads may be used in the pump (28) alone to achieve an adequate seal, especially at lower pressures with more viscous fluid.

2–64 UNF threading may be employed to achieve the fine control desired of the miniature screw pump. Different thread pitches and bore configurations may be used as well, such as 4–40 UNF (or similar metric sizes). In certain embodiments of the invention, the volume of fluid extruded from the pump may be approximately 10 nanoliters to 5 microliters of fluid per pump turn. Gradations on the pump housing, such as those on a micrometer screw gauge, may be provided, indicative of fluid delivered. Also, detent features may be provided to give tactile feedback to a user in turning the pump piston.

Some part of the exterior of the pump housing (34) may optionally have a milled outer surface (40). This facilitates gripping the member while turning piston (32) to advance it. The piston member may be turned by a screwdriver placed in optional slot (42) or with another tool set in a common interface. Still further, it may be desired to provide a knob or another interface at the piston member end for direct manual manipulation.

To use the inventive device, access is provided to the round window niche. This may be accomplished by providing a slit in the tympanic membrane or by entering the middle ear subcutaneously alongside the tympanic membrane or through other surgical means. Progress of the end of the catheter may be monitored by direct vision. Once the balloon (8) has been placed in the hollow of the round window niche (2), the pump (28) is actuated to fill the balloon to secure the end of the catheter in the round window niche. At this point a therapeutic agent such as an antibiotic e.g. gentamicin and/or a corticosteroid or other drug is delivered thought at least one delivery lumen (12). An external pump such as an osmotic pump, for example the Duros™ pump produced by Durect Corporation of California, may be used for this purpose. Alternately a pump may be mechanical, electrical, electromechanical or of any other suitable type. The drug is then allowed to pass onto and optionally through the round window membrane (4) as depicted in FIG. 3, effecting desired treatment for indications such as Meniere's disease, hearing loss, tinnitus, vertigo or other ear diseases. The drug may fill the space of the round window niche so that the drug is in contact with the round window membrane. If a second delivery lumen is provided, excess drug may be drained away via this lumen.

In certain embodiments, the invention may optionally include a delivery lumen that can be used for removing a fluid from the inner ear. Also, in certain embodiments, the invention may also include a means of illumination and/or visualization such as one or more fiber-optic cables that allows an operator to pass light through the catheter and there by illuminate and see beyond the distal end of the catheter, enabling visualization and aiding in positioning of the catheter. Also, in certain embodiments, the invention may encompass a catheter having a lumen that delivers a fluid used to flush the round window niche of the inner ear with a fluid, and a second lumen that drains fluid from the area of the round window niche. In certain embodiments the invention may include an electrode secured within the catheter which electrode may be used, as known in the art, to measure electrical signals produced in the ear, such as auditory evoked potentials.

Removal of the catheter is preferably achieved by first deflating the balloon prior to withdrawal. However, immediate retraction is also an option if need arises. Overall compliance in the system, particularly the inflation lumen and the balloon itself provides low contact stresses thus allowing removal without deflation if the need arises.

While the present invention has been described with reference to the specific embodiments thereof, it should be understood by those skilled in the art that various changes may be made and equivalents may be substituted without departing from the true spirit and scope of the invention. For instance, parallel lumen arrangements may be used, as may a single delivery lumen. In addition, many modifications may be made to adapt a particular situation, material, shape, configuration, composition of matter, process, process step or steps, to the objective, spirit and scope of the present invention. All such modifications are intended to be within the scope of the claims made hereafter.

What is claimed is:

1. An apparatus for delivery of a therapeutic agent to the round window of the inner ear, the apparatus comprising: an inflation lumen (22) having a proximal end and a distal end, and at least one delivery lumen (12) having a proximal end and a distal end, the distal end of the inflation lumen being in fluid communication with an expandable balloon member (8) wherein the expandable balloon member, when expanded, is adapted to fit securely within the round window niche of the inner ear, the proximal end of the inflation lumen being in fluid communication with a miniature screw pump (28), wherein the miniature screw pump comprises a piston (32), a housing (34) and a threaded interface (30) for driving the piston within the housing, and further wherein the distal end of the delivery lumen is positioned to allow delivery of the therapeutic agent to the round window of the inner ear when the balloon is secured within the round window niche.

2. The apparatus of claim 1 wherein the miniature screw pump (28) has a displacement of between about 0.5 microliters and 100 microliters.

3. The apparatus of claim 2 wherein the miniature screw pump (28) has a displacement of between about 1 microliter and 50 microliters.

4. The apparatus of claim 3 wherein the miniature screw pump (28) has a displacement of between about 1 microliter and 25 microliters.

5. The apparatus of claim 1 wherein the inflation lumen (22) contains a fluid and wherein balloon inflation is accomplished by displacement of the fluid by means of the miniature screw pump (28).

6. The apparatus of claim 5 wherein the fluid is a viscous fluid.

7. The apparatus of claim 6 wherein the viscous fluid is selected from the group consisting of: silicone, an oil, a sugar solution and a polymer.

8. A method for delivering a therapeutic agent to the round window of the inner ear, comprising introducing into the ear an apparatus, the apparatus comprising:

an inflation lumen (22) having a proximal end and a distal end, and at least one delivery lumen (12) having a proximal end and a distal end, the distal end of the inflation lumen being in fluid communication with an expandable balloon member (8), wherein the expandable balloon member, when expanded, is adapted to fit securely within the round window niche of the inner ear, the proximal end of the inflation lumen being in fluid communication with a miniature screw pump (28), wherein said miniature screw pump comprises a piston (32), a housing (34) and a threaded interface (30) for driving the piston within the housing, and further wherein the inflation lumen contains a fluid and wherein balloon inflation is accomplished by displacement of the fluid by means of the miniature screw pump, and wherein the distal end of the delivery lumen is positioned to allow delivery of the therapeutic agent to the round window of the inner ear when the balloon is secured within the round window niche, and, by means of the miniature screw pump, inflating the balloon to secure it within the round window niche of the inner ear, and delivering a therapeutic agent through the catheter to the round window of the inner ear.

9. The method of claim 8, wherein the miniature screw pump (28) has a displacement of between about 0.5 microliters and 100 microliters.

10. The method of claim 9, wherein the miniature screw pump (28) has a displacement of between about 1 microliter and 50 microliters.

11. The method of claim 10, wherein the miniature screw pump has a displacement of between about 1 microliter and 25 microliters.

12. The method of claim 8, wherein the fluid is a viscous fluid.

13. The method of claim 12 wherein the viscous fluid is selected from the group consisting of: silicone, an oil, a sugar solution and a polymer.

14. The method of claim 8 wherein the apparatus is retained in the ear for a period of greater than one day.

15. The method of claim 14 wherein the apparatus is retained in the ear for a period of greater than one week.

16. The method of claim 15 wherein the apparatus is retained in the ear for a period of greater than one month.

17. The method of claim 8 wherein the apparatus is retained in the ear for a period of greater than three months.

* * * * *